United States Patent
Jolidon et al.

(10) Patent No.: US 7,485,637 B2
(45) Date of Patent: Feb. 3, 2009

(54) BENZOYL-TETRAHYDROPIPERIDINE DERIVATIVES

(75) Inventors: Synese Jolidon, Blauen (CH); Robert Narquizian, St. Louis (FR); Roger David Norcross, Olsberg (CH); Emmanuel Pinard, Linsdorf (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 603 days.

(21) Appl. No.: 11/302,403

(22) Filed: Dec. 13, 2005

(65) Prior Publication Data
US 2006/0148797 A1 Jul. 6, 2006

(30) Foreign Application Priority Data
Jan. 4, 2005 (EP) ................... 05100027

(51) Int. Cl.
A61K 31/535 (2006.01)
C07D 413/10 (2006.01)
(52) U.S. Cl. ................... 514/235.5; 514/354; 544/124; 546/314
(58) Field of Classification Search .............. 514/235.5, 514/354; 544/124; 546/314
See application file for complete search history.

(56) References Cited

U.S. PATENT DOCUMENTS

| | | | |
|---|---|---|---|
| 3,933,802 | A | 1/1976 | Ferrini et al. |
| 4,122,083 | A | 10/1978 | Sundeen et al. |
| 4,244,871 | A | 1/1981 | Kosary et al. |
| 7,034,047 | B2 * | 4/2006 | Tobe et al. .......... 514/383 |
| 7,067,501 | B2 * | 6/2006 | Smith et al. .......... 514/85 |
| 7,427,612 | B2 * | 9/2008 | Alberati-Giani et al. .......... 514/217.05 |
| 7,429,585 | B2 * | 9/2008 | Jolidon et al. .......... 514/234.8 |
| 2004/0167166 | A1 | 8/2004 | Alberati-Giani et al. |
| 2005/0059668 | A1 | 3/2005 | Alberati-Giani et al. |
| 2005/0070539 | A1 | 3/2005 | Alberati-Giani et al. |
| 2005/0209241 | A1 | 9/2005 | Jolidon et al. |

FOREIGN PATENT DOCUMENTS

| | | |
|---|---|---|
| DE | 2533605 | 2/1977 |
| EP | 0 171 636 | 2/1985 |
| EP | 0 624 584 | 11/1994 |
| EP | 0 82 098 A | 2/1998 |
| WO | WO 99/44596 | 9/1999 |
| WO | WO 99/45011 | 9/1999 |
| WO | WO 02/22612 | 3/2002 |
| WO | WO 02/074774 | 9/2002 |
| WO | WO 03/004480 | 1/2003 |
| WO | WO 03/035602 | 5/2003 |
| WO | WO 2004/037800 | 5/2004 |
| WO | WO2007/060408 | * 5/2007 |

OTHER PUBLICATIONS

Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R., Cell vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. in Neurobiol. vol. 67, pp. 173-202 (2002).
Carlsson M. L., Neural Trans. vol. 105, pp. 525-535 (1998).
Kwong et al., Org. Lett. 4, pp. 581-584 (2002).
Kuwano et al., JOC 67, pp. 6479-6486 (2002).
Chem. Abstract XP-002299148.
Caulfield W. L. et al., Journal of Med. Chem. vol. 44(17) pp. 2679-2682 (2001).
Chem. Abstract XP-002299149.
Chemical Abstracts Service, 23. Apr. 2003, XP002308402, Database accession No. 2003: 2142911 Chemcats & Catalog: AsInExExpress Gold.
Chemical Abstracts Service, 6. Jun. 2003, XP002308481 & Database Chemcats.

(Continued)

Primary Examiner—Celia Chang
(74) Attorney, Agent, or Firm—George W. Johnston; Patricia S. Rocha-Tramaloni; Kimberly J. Prior

(57) ABSTRACT

The present invention relates to compounds of formula I

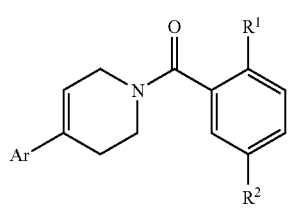

wherein $R^1$, $R^2$, and Ar; are as defined in the specification. The invention also provides pharmaceutically acceptable acid addition salts thereof and methods for the treatment of neurological and neuropsychiatric disorders, such as schizophrenia, cognitive impairment, and Alzheimer's disease.

21 Claims, No Drawings

OTHER PUBLICATIONS

Chemical Abstracts Service, 1. Jan. 2004, XP002308405, Database accession No. 2003:2872406 Chemcats & Catalog: Ambinter Stock Screening Collection.
Chemical Abstracts Service, 1. Jan. 2004, XP002308403, Database accession No. 2004:591813 & Catalog: Ambinter Stock Screening Collection.
Chemical Abstracts Service, 1. Jan. 2004, XP002308404, Database accession No. 2004:660630 & Catalog: Ambinter Screening Library.
Chemical Abstracts Service, XP002308978.
Chemical Abstracts Service, XP002308979; Chemcats No. 2003:1026314.
Chemical Abstracts Service, XP002308980; Chemcats No. 2001;2814605.
Chemical Abstracts Service, XP002308981; Chemcats No. 2002:2063001.
Chemical Abstracts Service, XP002308983; Chemcats No. 2003:1026533.
Chemical Abstracts Service, XP002308984; Chemcats No. 2002:2288893.
Chemical Abstracts Service, XP002308985; Chemcats No. 2003:709504.
Chemical Abstracts Service, XP002308986; Chemcats No. 2003:709503.
Chemical Abstracts Service, XP002308987; Chemcats No. 2003:709505.
Chemical Abstracts Service, XP002308988; Chemcats No. 2004:1498769.
Chemical Abstracts Service, XP002308989; Chemcats No. 2002:2386068.
Chemical Abstracts Service, XP002308990; Chemcats No. 2002:2894607.
Chemical Abstracts Service, XP002308991; Chemcats No. 2003:3342164.
Chemical Abstracts Service, XP002308992; Chemcats No. 2003:3345505.
Chemical Abstracts Service, XP002308993; Chemcats No. 2003:3346187.
Chemical Abstracts Service, XP002309007; Chemcats No. 2004:660630.
Abstract corresponding to Document B5-WO 03/035602.
Cabiddu et al., Journal of Organometallic Chemistry, 1991, 419(1-2) 1-8.
Collins, et al., J. Med. Chem. 1998, 41, p. 5037-5054.
Abstract corresponding to Document B10-DE2533605.

* cited by examiner

BENZOYL-TETRAHYDROPIPERIDINE DERIVATIVES

PRIORITY TO RELATED APPLICATIONS

This application claims the benefit of European Application No. 05100027.1, filed Jan. 4, 2005, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 2000, 28:325-33). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 2001, 5(4): 507-518; Nakazato A and Okuyama S, et al., 2000, Exp. Opin. Ther. Patents, 10(1): 75-98). This pharmacological approach poorly address negative and cognitive symptoms which are the best predictors of functional outcome (Sharma T., Br. J. Psychiatry, 1999, 174(suppl. 28): 44-51).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., 1999, Biol. Psychiatry, 45: 668-679 and refs. herein). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., 1999, Cell, 98: 427-436).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb D O, 1949, The organization of behavior, Wiley, NY; Bliss T V and Collingridge G L, 1993, Nature, 361: 31-39). Transgenic mice overexpressing the NMDA NR2B subunit exhibit enhanced synaptic plasticity and superior ability in learning and memory (Tang J P et al., 1999, Nature: 401-63-69).

Thus, if a glutamate deficit is implicated in the pathophysiology of schizophrenia, enhancing glutamate transmission, in particular via NMDA receptor activation, would be predicted to produce both anti-psychotic and cognitive enhancing effects. The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, 2002, Trends in Pharm. Sci., 23(8): 367-373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., 2001, Mol. Mem. Biol., 18: 13-20). Thus, one strategy to enhance NMDA receptor activity is to elevate the glycine concentration in the local microenvironment of synaptic NMDA receptors by inhibition of GlyT-1 transporter (Bergereon R. Et al., 1998, Proc. Natl. Acad. Sci. USA, 95: 15730-15734; Chen L et al., 2003, J. Neurophysiol., 89 (2): 691-703).

Glycine transporters inhibitors are suitable for the treatment of neurological and neuropsychiatric disorders. The majority of diseases states implicated are psychoses, schizophrenia (Armer R E and Miller D J, 2001, Exp. Opin. Ther. Patents, 11 (4): 563-572), psychotic mood disorders such as severe major depressive disorder, mood disorders associated with psychotic disorders such as acute mania or depression associated with bipolar disorders and mood disorders associated with schizophrenia, (Pralong E T et al., 2002, Prog. Neurobiol., 67: 173-202), autistic disorders (Carlsson M L, 1998, J. Neural Transm. 105: 525-535), cognitive disorders such as dementias, including age related dementia and senile dementia of the Alzheimer type, memory disorders in a mammal, including a human, attention deficit disorders and pain (Armer R E and Miller D J, 2001, Exp. Opin. Ther. Patents, 11 (4): 563-572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula I

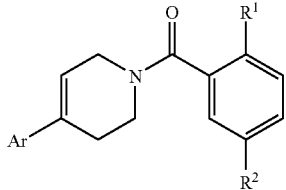

wherein
$R^1$ is a non aromatic heterocycle or OR';
R' is lower alkyl, lower alkyl substituted by halogen, or —$(CH_2)_n$-cycloalkyl;
$R^2$ is $NO_2$, CN or $SO_2R''$;
R" is lower alkyl;
Ar is phenyl, optionally substituted by halogen, cyano, lower alkyl substituted by halogen, or $SO_2R''$;
n is 0, 1 or 2;

and pharmaceutically acceptable acid addition salts thereof.

Furthermore, the invention includes all racemic mixtures, all their corresponding enantiomers and/or optical isomers. The invention also provides pharmaceutical compositions containing compounds of the invention and methods for the manufacture of such compounds and compositions. Compounds of formula I are good inhibitors of the glycine transporter 1 (GlyT-1), and have good selectivity to glycine transporter 2 (GlyT-2) inhibitors. The invention further provides methods for the treatment of diseases related to activation of NMDA receptors via Glyt-1 inhibition, such as psychoses, dysfunction in memory and learning, schizophrenia, dementia and other diseases in which cognitive processes are impaired, such as attention deficit disorders or Alzheimer's disease. The preferred indications using the compounds of the present invention are schizophrenia, cognitive impairment and Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-carbon chain containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "cycloalkyl" denotes a saturated carbon ring, containing from 3 to 7 carbon atoms, for example, cyclopropyl, cyclopentyl or cyclohexyl.

As used herein the term "non aromatic heterocycle" denotes a five or six membered heterocyclic ring, containing one or two heteroatoms, selected from the group consisting of O, N or S. Preferred rings are 1-pyrrolidine, 1-piperidine, 1-piperazine or 1-morpholine.

The term "halogen" denotes chlorine, iodine, fluorine and bromine.

As used herein the term "lower alkyl substituted by halogen" denotes an alkyl group as defined above, wherein at least one hydrogen atom is replaced by halogen, for example $CF_3$, $CHF_2$, $CH_2F$, $CH_2CF_3$ and the like.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

The present invention provides compounds of formula I

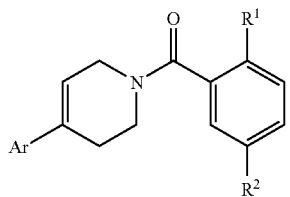

wherein
$R^1$ is a non aromatic heterocycle or OR';
R' is lower alkyl, lower alkyl substituted by halogen, or —$(CH_2)_n$-cycloalkyl;
$R^2$ is $NO_2$, CN or $SO_2R''$;
R" is lower alkyl;
Ar is phenyl, optionally substituted by halogen, cyano, lower alkyl substituted by halogen, or $SO_2R''$;
n is 0, 1 or 2;

and pharmaceutically acceptable acid addition salts thereof.

Preferred compounds of formula I are those, wherein $R^1$ is morpholine, for example the followings:

4-[1-(2-morpholin-4-yl-5-nitro-benzoyl)-1,2,3,6-tetrahydro-pyridin-4-yl]benzonitrile, (5-methanesulfonyl-2-morpholin-4-yl-phenyl)-[4-(4-trifluoromethyl-phenyl)-3,6dihydro-2H-pyridin-1-yl]-methanone and

[4-(4-methanesulfonyl-phenyl)-3,6-dihydro-2H-pyridin-1-yl]-(2-morpholin-4-yl-5-nitro-phenyl)-methanone Within this group, preferred compounds are those in which $R^2$ is $NO_2$. Also preferred are those compounds where $R^2$ is $SO_2R''$.

Further preferred are compounds, wherein $R^1$ is —O-lower alkyl substituted by halogen, which compound is

[5-methanesulfonyl-2-(2,2,2-trifluoro-ethoxy)-phenyl]-[4-(4-trifluoromethyl-phenyl)3,6-dihydro-2H-pyridin-1-yl]-methanone.

Further preferred are compounds, wherein $R^1$ is —O-lower alkyl, which compound is 3-[4-(4-chloro-phenyl)-3,6-dihydro-2H-pyridine-1-carbonyl]-4-isopropoxy-benzonitrile.

Preferred compounds of formula I are further those, wherein $R^1$ is —O—$(CH_2)_n$-cycloalkyl, for example the following compounds:

(2-cyclopentyloxy-5-methanesulfonyl-phenyl)-[4-(4-methanesulfonyl-phenyl)-3,6-dihydro-2H-pyridin-1-yl]-methanone and

[4-(4-chloro-phenyl)-3,6-dihydro-2H-pyridin-1-yl]-(2-cyclopropylmethoxy-5-methanesulfonyl-phenyl)-methanone.

Other preferred compounds of formula I are those where $R^2$ is $NO_2$. Also preferred are compounds where $R^2$ is cyano.

Further preferred are compounds where $R^2$ is $SO_2R''$. In particular, those in which Ar is phenyl substituted by either halogen or $SO_2R''$.

Other preferred compounds are those wherein Ar is unsubsituted phenyl. Also preferred are compounds where Ar is phenyl substituted by lower alkyl substituted by halogen. Further preferred compounds are those where Ar is phenyl substituted by $SO_2R''$. Preferred compounds include those where Ar is phenyl substituted by cyano, as well as those where Ar is phenyl substituted by halogen.

The present compounds of formula I and their pharmaceutically acceptable salts can be prepared by methods known in the art, for example, by the process described below, which process comprises a) reacting a compound of formula

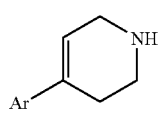

II with a compound of formula

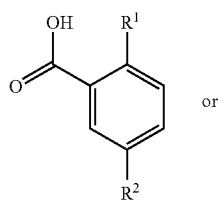

III-1 or

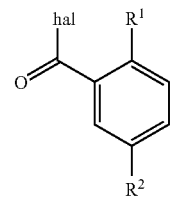

III-2 in the presence of an activating agent, such as TBTU (2-(1H-benzotriazole-1-yl)-1,1,3,3-tetramethyluroniumtetrafluoroborate), for compounds of formula III-1, to produce a compound of formula

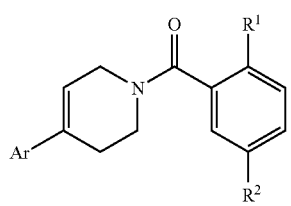

I wherein hal is a halogen atom, such as chloride, and Ar, $R^1$ and $R^2$ are as defined above, and if desired, converting the compounds obtained into pharmaceutically acceptable acid addition salts thereof.

The compounds of formula I can be prepared in accordance with process variant a) and with the following scheme 1. All starting materials are either commercially available, described in the literature or can be prepared by methods well known in the art.

The following abbreviation has been used:

TBTU=2-(1H-Benzotriazole-1-yl)-1,1,3,3-tetramethyluronium tetrafluoroborate

Scheme 1

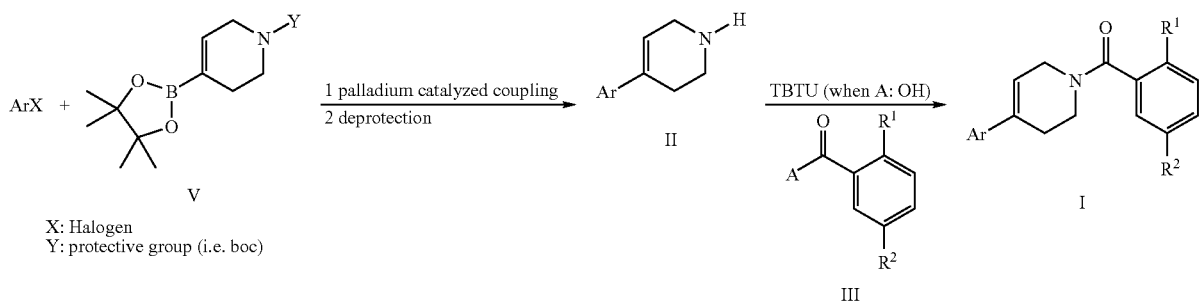

X: Halogen
Y: protective group (i.e. boc)

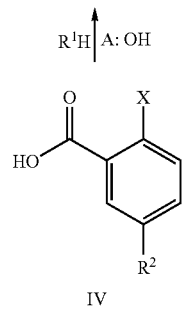

IV

Compounds of formula I can be prepared by reacting 4-aryl-substituted-1,2,3,6-tetrahydro-pyridine derivative of formula II with a corresponding acid of formula III (A: OH) in the presence of an activating agent, like TBTU, or with a corresponding activated acid of formula III (A: Cl). The acid of formula III can be prepared by reaction of an acid of formula IV with a nucleophile of formula $R^1H$. 4-aryl-substituted-1,2,3,6-tetrahydro-pyridine derivatives of formula II can be prepared under Suzuki conditions (*Eastwood et al. tetrahedron Letters* (2000), 41, (19), 3705-3708) by reacting boronic ester V with ArX in the presence of palladium catalyst, followed by cleavage of the protective group as shown in scheme 1. The protective group is typically tert-butoxycarbonyl (Boc).

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically acceptable addition salts possess valuable pharmacological properties. Specifically, it has been found that the compounds of the present invention are good inhibitors of the glycine transporter I (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 µM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The preferred compounds show an $IC_{50}$ (µM) at GlyT-1<0.9.

| Example No. | $IC_{50}$ (µM) |
|---|---|
| 1 | 0.803 |
| 2 | 0.432 |
| 3 | 0.270 |
| 4 | 0.122 |
| 5 | 0.232 |
| 6 | 0.251 |
| 7 | 0.870 |
| 8 | 0.201 |
| 9 | 0.28 |
| 10 | 0.056 |

The present invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

Compounds of formula I are good inhibitors of the glycine transporter 1 (GlyT-1), and have good selectivity to glycine transporter 2 (GlyT-2) inhibitors. The invention further provides methods for the treatment of diseases related to activation of NMDA receptors via Glyt-1 inhibition, such as psychoses, dysfunction in memory and learning, schizophrenia, dementia and other diseases in which cognitive processes are impaired, such as attention deficit disorders or Alzheimer's disease. In particular, the present invention provides a method for treating schizophrenia, which comprises administering a therapeutically effective amount of a compound of formula I or a pharmaceutically acceptable salt thereof. The invention also provides a method of treating cognitive impairment, which comprises administering a therapeutically effective amount of a compound of formula I or a pharmaceutically acceptable salt thereof. The invention further provides a method for the treatment of Alzheimer's disease, which comprises administering a therapeutically effective amount of a compound of formula I or a pharmaceutically acceptable salt thereof.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

|  |  | mg/tablet | | | |
| --- | --- | --- | --- | --- | --- |
| Item | Ingredients | 5 mg | 25 mg | 100 mg | 500 mg |
| 1. | Compound of formula IA or IB | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
|  | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|  |  | mg/capsule | | | |
| --- | --- | --- | --- | --- | --- |
| Item | Ingredients | 5 mg | 25 mg | 100 mg | 500 mg |
| 1. | Compound of formula IA or IB | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
|  | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following examples illustrate the present invention without limiting it. All temperatures are given in degree Celsius.

All starting materials are either commercially available, described in the literature or can be prepared by methods well known in the art.

EXAMPLE 1

(2-Morpholin-4-yl-5-nitro-phenyl)-(4-phenyl-3,6-dihydro-2H-pyridin-1-yl)-methanone

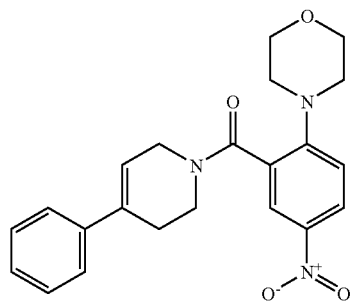

1a: 2-Morpholin-4-yl-5-nitro-benzoic acid

To a solution of 2-fluoro-5-nitrobenzoic acid (4.86 g, 26.2 mmol) in dioxane (50 ml) was added morpholine (11.5 ml). The mixture was stirred at room temperature for 2 hours. The solvent was removed in vacuo. The residue was dissolved in water and the mixture was acidified with HCl 2N. The solid was filtered, washed with water and dried to provide the title compound (6.2 g, 93%) as a yellow solid, MS (m/e): 251.2 (M−H, 100%).

1b: 2-Morpholin-4-yl-5-nitro-benzoyl chloride

To a suspension of 2-morpholin-4-yl-5-nitro-benzoic acid (4.0 g, 16 mmol) in toluene were added 2 drops of DMF and thionylchloride (5.7 ml, 79.3 mmol). The mixture was heated to 80° C. for 50 minutes. The solvent was removed in vacuo, and the resulting solid was stirred in ether, filtered and dried to provide the title compound (4.0 g, 93%) as a yellow solid.

1c: (2-Morpholin-4-yl-5-nitro-phenyl)-(4-phenyl-3,6-dihydro-2H-pyridin-1-yl)-methanone A mixture of 40.6 mg (0.15 mmol) of 2-morpholin-4-yl-5-nitro-benzoyl chloride, 29 mg (0.18 mmol) 4-phenyl-1,2,3,6-tetrahydro-pyridine (commercial) and 62.5 ul (0.45 mmol) NEt₃ in 1 ml DCM was stirred at room temperature for 16 h. After evaporation of the volatiles the residue was taken up in 1 ml CH₃CN/DMF/HCOOH 3/5/2 and subjected to preparative HPLC purification on reversed phase eluting with an acetonitrile/water gradient to yield after evaporation the title compound.
MS (m/e): 394.1 (MH⁺, 100%)

EXAMPLE 2

[4-(4-Chloro-phenyl)-3,6-dihydro-2H-pyridin-1-yl]-(2-morpholin-4-yl-5-nitrophenyl) methanone

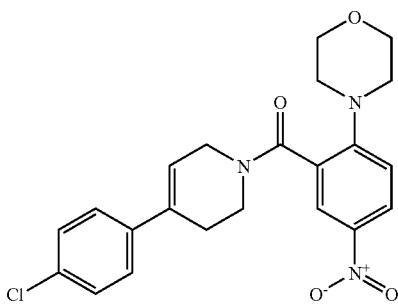

According to the procedure described for the synthesis of example 1, the title compound has been synthesized from 2-morpholin-4-yl-5-nitro-benzoyl chloride and 4-(4-Chloro-phenyl)-1,2,3,6-tetrahydro-pyridine hydrochloride (commercial). MS (m/e): 428.1 (MH⁺, 100%)

EXAMPLE 3

4-[1-(2-Morpholin-4-yl-5-nitro-benzoyl)-1,2,3,6-tetrahydro-pyridin-4-yl]benzonitrile

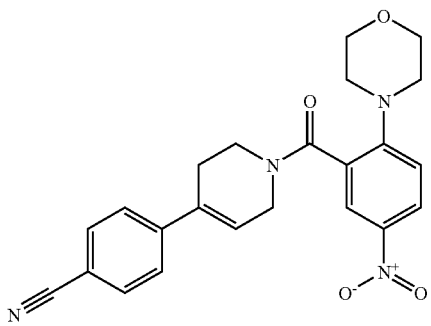

According to the procedure described for the synthesis of example 1, the title compound has been synthesized from 2-morpholin-4-yl-5-nitro-benzoyl chloride and 4-(1,2,3,6-Tetrahydro-pyridin-4-yl)-benzonitrile (CAS: 460365-22-4). MS (m/e): 417.0 (M−H, 100%)

EXAMPLE 4

[5-Methanesulfonyl-2-(2,2,2-trifluoro-ethoxy)-phenyl]-[4-(4-trifluoromethyl-phenyl)3,6-dihydro-2H-pyridin-1-yl]-methanone

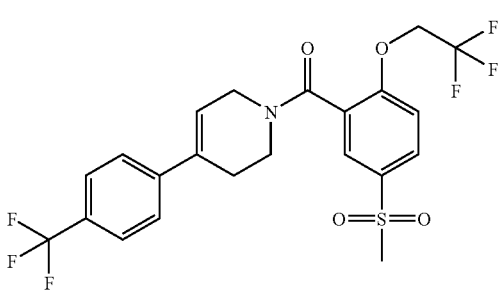

4a: 2-Chloro-5-sulfino-benzoic acid

A solution of 33.59 g (267 mmol) sodium sulfite in 100 ml water at 0° C. is treated with 21.2 g (89 mmol) 2-chloro-5-fluorosulfonyl-benzoic acid and 26.6 ml of a 10 M aqueous NaOH solution (267 mmol). The mixture was allowed to stir for 3 h at room temperature, acidified with HCl conc. (pH=4) and water was removed under vacuum. Methanol was added, the precipitate filtered off and the filtrate concentrated. Methanol and diethylether were added and the precipitate was filtered off washed with ether and dried to yield 15 g (76.5%) of the title compound as white gum. MS (m/e): 219.1 (M−H, 100%)

4b: 2-Chloro-5-methanesulfonyl-benzoic acid

A mixture of 1 g (4 mmol) 2-Chloro-5-sulfino-benzoic acid in 20 ml methanol and 20 ml water was treated with 10N NaOH to pH=9 before adding 1.7 g (12 mmol) methyliodide. The mixture was heated for 48 h to 80° C. with occasional addition of NaOH to maintain pH=9. After removal of all volatiles HCl conc. was added and the mixture was extracted with ethyl acetate. The combined organic layers were dried with MgSO₄ and evaporated to dryness. The residue was taken up in methanol and subjected to reversed phase HPLC purification eluting with an acetonitrile/water gradient to yield after evaporation of the product fractions 323 mg (34%) of the title compound. MS (m/e): 233.0 (M−H, 100%)

4c: 5-methanesulfonyl-2-(2,2,2-trifluoro-ethoxy)-benzoic acid

A mixture of 2.13 mmol 2-chloro-5-methanesulfonyl-benzoic acid, 0.64 mmol Cu(I)Br in 5 ml NEt₃ and 25 ml 2,2,2-trifluoro-ethanol was heated to 120° C. for 16 h in a sealed tube. The volatiles were removed under vacuum and the residue was taken up in 70 ml 1N HCl. Extraction with ethyl acetate drying of the combined organic fractions and evaporation yielded a residue which was purified by reversed phase preparative HPLC eluting with an acetonitrile/water gradient. Evaporation of the product fractions yielded the title compound. MS (m/e): 297.0 (M−H, 100%)

4d: 4-(4-Trifluoromethyl-phenyl)-3,6-dihydro-2H-pyridine-1-carboxylic acid tert-butyl ester To a solution of 0.97 mmol 4-(4,4,5,5-tetramethyl-[1,3,2]dioxaborolan-2-yl)-3,6-dihydro-2H-pyridine-1-carboxylic acid tert-butyl ester (CAS: 286961-14-6) in 6 ml dimethylformamide, 2.91 mmol potassium carbonate, 1.02 mmol p-bromobenzotrifluoride, and 0.06 mmol dichlor(1,1' bis(diphenylphosphino)ferrocene) palladium(II)dichloromethane complex were successively added. The reaction was then stirred at 80° C. for 6 hours, concentrated in vacuo and purified by column chromatography (SiO$_2$, 20 g, heptane), to give the title compound. MS (m/e): 271.1 (M-isobuthylene)

4e: 4-(4-Trifluoromethyl-phenyl)-1,2,3,6-tetrahydropyridine

A mixture of 0.52 mmol 4-(4-trifluoromethyl-phenyl)-3,6-dihydro-2H-pyridine-1-carboxylic acid tert-butyl ester in 2 ml dichloromethane was treated with 0.2 ml trifluoroacetic acid. The mixture was stirred at 40° C. for 3 hrs then concentrated and treated with water/NaOH and extracted with dichloromethane. The combined organic phases were washed with saturated NaCl, dried with MgSO$_4$ and evaporated to yield the title compound. MS (m/e): 228.3 (MH$^+$, 100%)

4f: 5-Methanesulfonyl-2-(2,2,2-trifluoro-ethoxy)-phenyl]-[4-(4-trifluoromethyl-phenyl)3,6-dihydro-2H-pyridin-1-yl]-methanone To a solution of 0.17 mmol 5-methanesulfonyl-2-(2,2,2-trifluoro-ethoxy)-benzoic acid in 0.75 ml dimethylformamide, 0.19 mmol TBTU, 0.855 mmol N-ethyldiisopropylamine and 0.205 mmol 4-(4-trifluoromethyl-phenyl)-1,2,3,6-tetrahydro-pyridine were successively added. The reaction was then stirred at RT for 45 min., concentrated in vacuo and purified by column chromatography (SiO$_2$, 10 g, heptane, ethylacetate 0 to 100%), to give the title compound. MS (m/e): 508.6 (MH$^+$, 100%)

EXAMPLE 5

(5-Methanesulfonyl-2-morpholin-4-yl-phenyl)-[4-(4-trifluoromethyl-phenyl)-3,6 dihydro-2H-pyridin-1-yl]-methanone

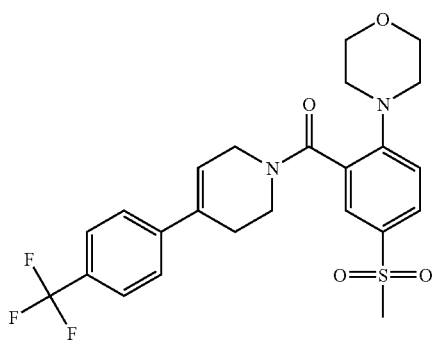

5a: 5-Methanesulfonyl-2-morpholin-4-yl-benzoic acid

A mixture of 163.8 mg (0.7 mmol) 2-chloro-5-methanesulfonyl-benzoic acid (example 4 step b) in 2 ml morpholine was heated for 16 h to 100° C. After evaporation of all volatiles the residue was taken up in 2 ml methanol/formic acid 3/1 and subjected to reversed phase HPLC purification eluting with an acetonitrile/water gradient to yield after evaporation of the product fractions the title compound. MS (m/e): 284.1 (M-H, 100%)

5b: (5-Methanesulfonyl-2-morpholin-4-yl-phenyl)-[4-(4-trifluoromethyl-phenyl)-3,6dihydro-2H-pyridin-1-yl]-methanone According to the procedure described for the synthesis of example 4, step f, the title compound has been synthesized from 5-Methanesulfonyl-2-morpholin-4-yl-benzoic acid and 4-(4-Trifluoromethyl-phenyl)-1,2,3,6-tetrahydro-pyridine. MS (m/e): 495.4 (MH$^+$, 100%)

EXAMPLE 6

[4-(4-Methanesulfonyl-phenyl)-3,6-dihydro-2H-pyridin-1-yl]-(2-morpholin-4-yl-5-nitro-phenyl)-methanone

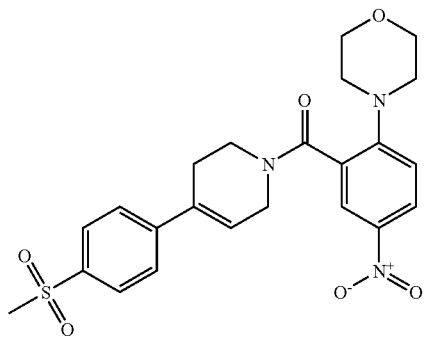

6a: 4-(4-Methanesulfonyl-phenyl)-1,2,3,6-tetrahydro-pyridine

The title compound has been synthesized from 4-(4,4,5,5-tetramethyl-[1,3,2]dioxaborolan-2-yl)-3,6-dihydro-2H-pyridine-1-carboxylic acid tert-butyl ester and 4-bromomethyl-sulfone following procedures described in example 4 step d and e. MS (m/e): 336.0 (M-H, 100%)

6b: [4-(4-Methanesulfonyl-phenyl)-3,6-dihydro-2H-pyridin-1-yl]-(2-morpholin-4-yl-5-nitro-phenyl)-methanone According to the procedure described for the synthesis of example 4, step f, the title compound has been synthesized from 2-Morpholin-4-yl-5-nitro-benzoic acid and 4-(4-Methanesulfonyl-phenyl)-1,2,3,6-tetrahydro-pyridine. MS (m/e): 470.1 (M-H, 100%)

EXAMPLE 7

(2-Isopropoxy-5-methanesulfonyl-phenyl)-[4-(4-methanesulfonyl-phenyl)-3,6-dihydro-2H-pyridin-1-yl]-methanone

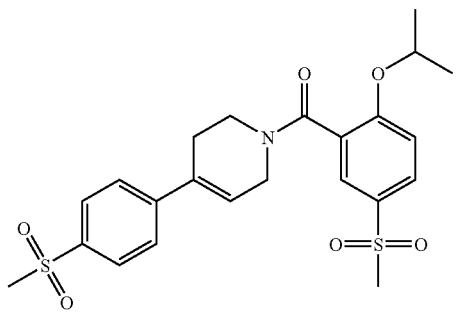

7a: 2-Isopropoxy-5-methanesulfonyl-benzoic acid

According to the procedure described for the synthesis of example 4, step c, the title compound has been synthesized from 2-chloro-5-methanesulfonyl-benzoic acid and isopropanol. MS (m/e): 257.0 (M−H, 100%)

7b: (2-Isopropoxy-5-methanesulfonyl-phenyl)-[4-(4-methanesulfonyl-phenyl)-3,6-dihydro-2H-pyridin-1-yl]-methanone According to the procedure described for the synthesis of example 4, step f, the title compound has been synthesized 2-isopropoxy-5-methanesulfonyl-benzoic acid and 4-(4-Methanesulfonyl-phenyl)-1,2,3,6-tetrahydro-pyridine. MS (m/e): 495.4 (M+NH$_4^+$, 100%)

EXAMPLE 8

(2-Cyclopentyloxy-5-methanesulfonyl-phenyl)-[4-(4-methanesulfonyl-phenyl)-3,6-dihydro-2H-pyridin-1-yl]-methanone

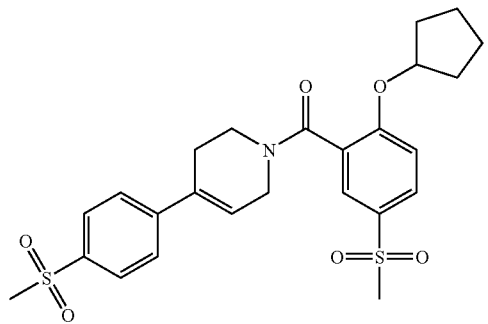

8a: 2-Cyclopentyloxy-5-methanesulfonyl-benzoic acid

According to the procedure described for the synthesis of example 4, step c, the title compound has been synthesized from 2-chloro-5-methanesulfonyl-benzoic acid and cyclopentanol. MS (m/e): 282.9 (M−H, 100%)

8b: (2-Cyclopentyloxy-5-methanesulfonyl-phenyl)-[4-(4-methanesulfonyl-phenyl)-3,6-dihydro-2H-pyridin-1-yl]-methanone According to the procedure described for the synthesis of example 4, step f, the title compound has been synthesized from 2-cyclopentyloxy-5-methanesulfonyl-benzoic acid and 4-(4-Methanesulfonyl-phenyl)-1,2,3,6-tetrahydro-pyridine. MS (m/e): 503.9 (M$^+$, 100%)

EXAMPLE 9

3-[4-(4-Chloro-phenyl)-3,6-dihydro-2H-pyridine-1-carbonyl]-4-isopropoxy-benzonitrile

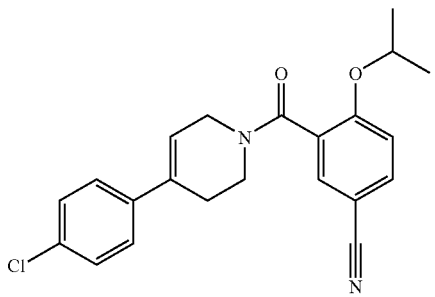

According to the procedure described for the synthesis of example 4, step f, the title compound has been synthesized from 5-cyano-2-isopropoxy-benzoic acid (CAS: 845616-14-0) and 4-(4-chloro-phenyl)-1,2,3,6-tetrahydro-pyridine hydrochloride (commercial). MS (m/e): 381.1 (MH$^+$, 100%).

EXAMPLE 10

[4-(4-Chloro-phenyl)-3,6-dihydro-2H-pyridin-1-yl]-(2-cyclopropylmethoxy-5-methanesulfonyl-phenyl)-methanone

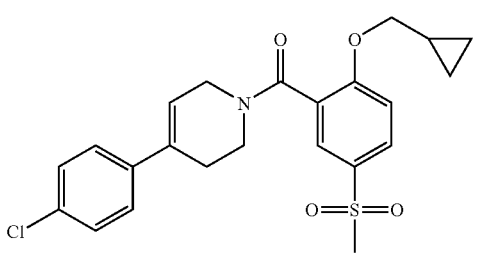

According to the procedure described for the synthesis of example 4, step f, the title compound has been synthesized from 2-cyclopropylmethoxy-5-methanesulfonyl-benzoic acid (CAS: 845616-03-7) and 4-(4-chloro-phenyl)-1,2,3,6-tetrahydro-pyridine hydrochloride (commercial). MS (m/e): 446.0 (MH$^+$, 100%).

The invention claimed is:
1. A compound of formula I

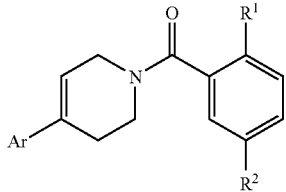

wherein
R¹ is a non aromatic heterocycle or OR';
R' is lower alkyl, lower alkyl substituted by halogen, or —(CH₂)$_n$-cycloalkyl;
R² is NO₂, CN or SO₂R";
R" is lower alkyl;
Ar is phenyl, optionally substituted by halogen, cyano, lower alkyl substituted by halogen, or SO₂R";
n is 0, 1 or 2;
or a pharmaceutically acceptable acid addition salt thereof.

2. A compound of claim 1, wherein R¹ is morpholine.
3. A compound of claim 2, wherein R² is NO₂.
4. A compound of claim 2, wherein R² is SO₂R".
5. A compound of claim 2, selected from the group consisting of
4-[1-(2-morpholin-4-yl-5-nitro-benzoyl)-1,2,3,6-tetrahydro-pyridin-4-yl]benzonitrile, (5-methanesulfonyl-2-morpholin-4-yl-phenyl)-[4-(4-trifluoromethyl-phenyl)-3,6dihydro-2H-pyridin-1-yl]-methanone,
[4-(4-methanesulfonyl-phenyl)-3,6-dihydro-2H-pyridin-1-yl]-(2-morpholin-4-yl-5-nitrophenyl)-methanone,
(2-Morpholin-4-yl-5-nitro-phenyl)-(4-phenyl-3,6-dihydro-2H-pyridin-1-yl)-methanone and
[4-(4-Chloro-phenyl)-3,6-dihydro-2H-pyridin-1-yl]-(2-morpholin-4-yl-5-nitrophenyl)methanone.
6. A compound of claim 1, wherein R¹ is —O-lower alkyl substituted by halogen.
7. A compound of claim 4, which compound is
[5-methanesulfonyl-2-(2,2,2-trifluoro-ethoxy)-phenyl]-[4-(4-trifluoromethyl-phenyl)3,6-dihydro-2H-pyridin-1-yl]-methanone.
8. A compound of claim 1, wherein R¹ is —O-lower alkyl.
9. A compound of claim 6, selected from the group consisting of
3-[4-(4-chloro-phenyl)-3,6-dihydro-2H-pyridine-1-carbonyl]-4-isopropoxy-benzonitrile and
(2-Isopropoxy-5-methanesulfonyl-phenyl)-[4-(4-methanesulfonyl-phenyl)-3,6-dihydro-2H-pyridin-1-yl]-methanone.
10. A compound of claim 1, wherein R¹ is —O—(CH₂)$_n$-cycloalkyl.
11. A compound of claim 8, selected from the group consisting of
(2-cyclopentyloxy-5-methanesulfonyl-phenyl)-[4-(4-methanesulfonyl-phenyl)-3,6-dihydro-2H-pyridin-1-yl]-methanone and
[4-(4-chloro-phenyl)-3,6-dihydro-2H-pyridin-1-yl]-(2-cyclopropylmethoxy-5-methanesulfonyl-phenyl)-methanone.
12. A compound of claim 1, wherein R² is NO₂.
13. A compound of claim 1, wherein R² is cyano.
14. A compound of claim 1, wherein R² is SO₂R".
15. A compound of claim 14, wherein Ar is phenyl substituted by halogen or SO₂R".
16. A compound of claim 1, wherein Ar is phenyl.
17. A compound of claim 1, wherein Ar is phenyl substituted by lower alkyl substituted by halogen.
18. A compound of claim 1, wherein Ar is phenyl substituted by SO₂R".
19. A compound of claim 1, wherein Ar is phenyl substituted by cyano.
20. A compound of claim 1, wherein Ar is phenyl substituted by halogen.
21. A pharmaceutical composition comprising a therapeutically effective amount of a compound of formula I

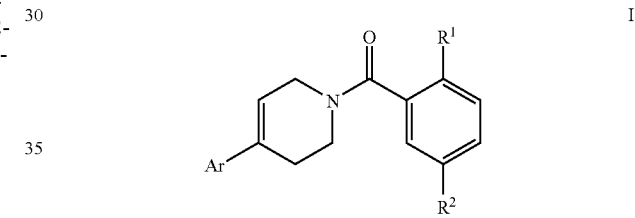

wherein
R¹ is a non aromatic heterocycle or OR';
R' is lower alkyl, lower alkyl substituted by halogen, or —(CH₂)$_n$-cycloalkyl;
R² is NO₂, CN or SO₂R";
R" is lower alkyl;
Ar is phenyl, optionally substituted by halogen, cyano, lower alkyl substituted by halogen, or SO₂R";
n is 0, 1 or 2;
or a pharmaceutically acceptable acid addition salt thereof and a pharmaceutically acceptable carrier.

* * * * *